United States Patent [19]

Frazier

[11] 4,402,669

[45] Sep. 6, 1983

[54] ORTHODONTIC SAFETY HEADGEAR

[75] Inventor: Paul D. Frazier, Rockville, Md.

[73] Assignee: Northwest Orthodontics, Inc., Seattle, Wash.

[21] Appl. No.: 78,686

[22] Filed: Sep. 25, 1979

Related U.S. Application Data

[63] Continuation of Ser. No. 703,828, Jul. 9, 1976, Pat. No. 4,215,983.

[51] Int. Cl.³ .............................................. A61C 7/00
[52] U.S. Cl. ......................................................... 433/5
[58] Field of Search ............................................. 433/5

[56] References Cited

U.S. PATENT DOCUMENTS

| 3,126,729 | 3/1964 | Leopoldi | 24/215 |
| 3,890,800 | 6/1975 | Montague | 24/201 TR |
| 4,155,161 | 9/1978 | Armstrong | 433/5 |

Primary Examiner—Robert Peshock
Attorney, Agent, or Firm—Robert W. Beach; Ward Brown

[57] ABSTRACT

An orthodontic headgear appliance having a safety system which includes force-adjusting mechanism for the headgear tensioning apparatus, a system for selectively setting limits for travel of the facebow during orthodontic treatment and a disconnecting system for disconnecting the facebow from the headgear tensioning apparatus when a forward force on the facebow exceeding a predetermined value continues to be applied after the travel limit is reached.

12 Claims, 9 Drawing Figures

ORTHODONTIC SAFETY HEADGEAR

CROSS-REFERENCE

This application is a continuation of my application Ser. No. 703,828 filed July 9, 1976 for Orthodontic Headgear Appliance Safety System which issued on Aug. 5, 1980 as U.S. Pat. No. 4,215,983.

BACKGROUND OF THE INVENTION

Field of the Invention

This application relates to orthodontic appliances mounted on the head exteriorly of the mouth for applying to a jaw an orthodontic correcting force usually through a device within the mouth.

Problem

Recent incidents in the field of orthodontics have made practitioners aware of safety hazards surrounding the use of various equipment. Especially potentially hazardous are extraoral appliances, i.e., those worn outside the mouth or in conjunction with equipment outside the mouth. In particular, facebows and low and high pull headgear have been found to be a source of potential injury to the patient, since such appliances have heretofore been designed so that undesirable pulling of the facebow away from the patient's mouth "loads" the appliance in much the same manner as a slingshot. Additionally, if the ends of the inner bow are drawn sufficiently far forward, they will slip out of the buccal tubes usually employed to support them and become misaligned with the tube openings, thereby presenting themselves as a pair of pointed, dangerous protrusions. If the facebow is pulled out sufficiently, the ends of the inner bow may be in a position to do serious damage to the inner mouth, tongue, gums or even the lips, face and eyes. At least one such incident has been reported which resulted in blinding the patient.

Prior Art

Prior art solutions to the problem of eliminating dangers associated with undesired tampering with the facebow or undesirable pulling on the headgear tensioning means include various methods, depending upon the type of tensioning apparatus being used (spring, rubber band or elastic strap) and upon the individual preference of the orthodontist. One approach is to permanently tie the inner bow in place with steel ligature wire. This method presents some hygiene problems but causes more concern because undesired pulling could cause the facebow to be severely deformed. If the patient should continue wearing a deformed facebow, it could cause harm to the patient in addition to being detrimental to the intended orthodontic treatment.

Because of the obvious disadvantages and dangers of permanently affixing the inner bow to the buccal tubes, removal systems which avoid the dangers enumerated above are much more desirable. Several removable systems are presently available to the orthodontic practitioner, including but not limited to the following:

One removable headgear system, described in U.S. Pat. No. 3,903,604, uses two different devices for locking the inner bow into the buccal tube. These mechanisms appear to satisfy the requirement that the device be capable of selective removal by either the orthodontist or the patient; however, the apparatus described is complex, expensive to manufacture and does not permit adjusting the length of the inner bow members for different patients. This presents a significant manufacturing problem and an inventory problem for the practitioner, since a very large selection of sizes is required in order to accomodate the average size distribution of patients.

A second approach attempts to limit extension of the tensioning means. While theoretically intended to limit the travel of the inner bow members in the bucca tubes, the practical result is at best confinement of the inner bow members to the oral cavity. These devices are of limited value because they do not prohibit undesired removal of the inner bow members from the buccal tube; the serious danger of a "slingshot" effect caused by the tensioning means propelling the ends of the facebow into soft tissues of the oral cavity is thus not eliminated. The reason for the failure of these travel limiting devices is the fact that it is impossible to eliminate displacement of the soft tissues of the patient's neck or to control the angle of the patient's head. Both of these factors influence the amount of slack in the tensioning members of the device in relationship to their connection to the outer members of the facebow. These devices may actually be more dangerous because of the false sense of security they provide.

A third approach to assure safety of headgear devices by preventing undesired removal of the bow members is presently available to the profession and provides a breakway mechanism between the tensioning means and the facebow. This particular mechanism is designed to function on a spring tensioning system and is described in Armstrong U.S. Pat. No. 4,115,921. The major advantage of this safety means is that the "slingshot" effect and permanent damage to the semi-rigid portions of the apparatus are both effectively prevented.

Objects of the Invention

It is a general object of this invention to provide safety disengaging devices for use with various types of headgear tensioning systems.

Other objects of the present invention will become apparent to those skilled in the art upon further study of the specification and appended claims.

Summary of the Invention

The above object of the present invention is attained in one aspect thereof by providing an orthodontic headgear tensioning apparatus for use with an orthodontic facebow, comprising;

an elastic neckband;

means for limiting the expansion travel of the elastic neckband;

facebow coupling means securely attached to each end of the elastic neckband; and disconnect means normally connected between each of said coupling means and the facebow outer bow ends for disconnecting from said coupling means when a pulling force persists on the facebow after said travel limiting means has limited the expansion travel of the elastic neckband.

DETAILED DESCRIPTION

In accordance with the present invention, a disconnecting attachment system is provided which is designed to attach to the end of the facebow outer member providing means whereby, when used in conjunction with an elastic neckstrap equipped with standard metal end fasteners and a special stretch-limiting device, it will disconnect when improperly pulled. Since this disconnecting device is located at the end of the outer bow, it also conveniently functions in conjunction with rubber band tensioned force means equipped with a special stretch limiting device interposed between them and the non-elastic neckstrap or headcap and the facebow member.

The presently preferred devices of the present invention provide efficient and reliable means for assuring safely limited resilient neckstraps, rubber band biased neckstraps or headcap appliances. The travel-limiting features are particularly important because of the necessity to activate the disconnecting mechanisms to prevent loading the headgear-tensioning systems as dangerous slingshot weapons. Additionally, in association with the stretch-limiting features, provision is made for disconnecting the tensioning system if it is improperly or inadvertently disengaged.

Figure 1:
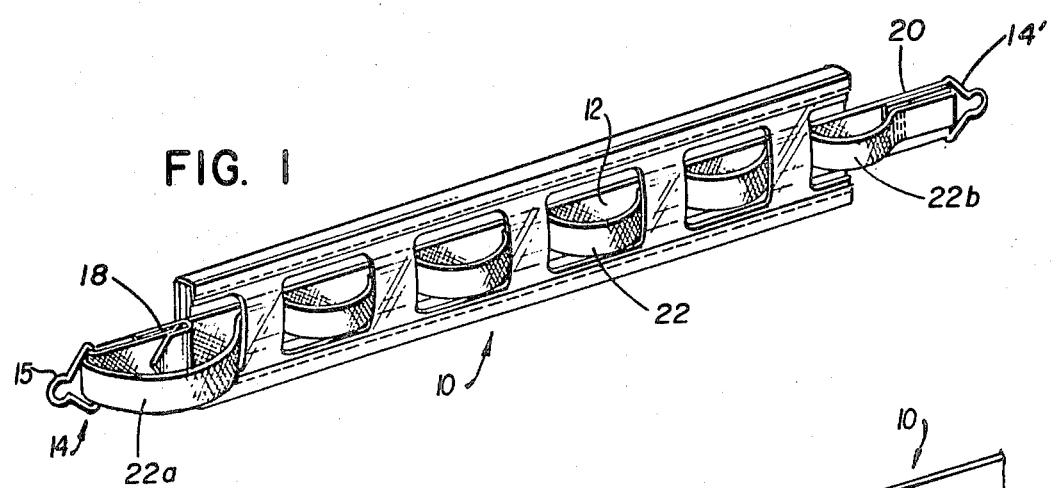
FIG. 1 is a perspective of an elastic orthodontic headgear neckstrap embodying a travel limiting means and adapted for use with a safety disconnect means of the present invention.
Figure 2:
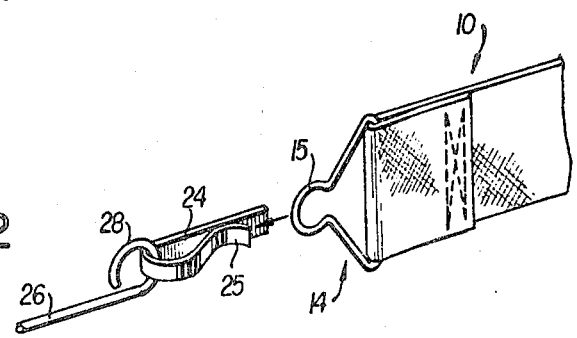
FIG. 2 is an enlarged perspective of a safety disconnect means useful with the neckstrap of FIG. 1.
Figure 3:
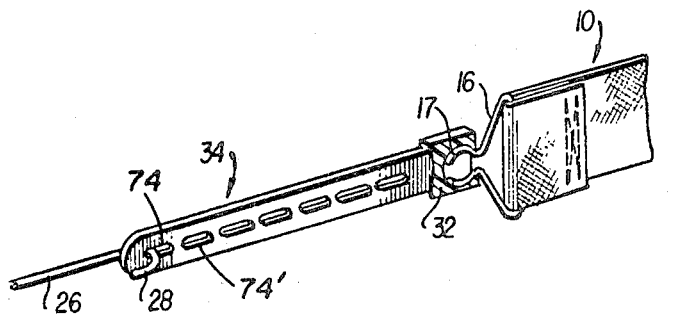
FIG. 3 is a perspective, partially in cross-section, showing another safety disconnect means useful with the neckstrap of FIG. 1 attached to a travel limiting and tension adjustment means on an orthodontic appliance.

Referring now to the drawings, FIG. 1 shows an orthodontic headgear neckstrap 10 which includes a strap 12 made of a resilient material, the ends of which are looped around connecting members 14 and 14' and attached to end members 18 and 20. It is understood that more than one adjustment member 18 may be used if desired. Member 18 is of a typical adjustment buckle configuration having projections which engage the strap material, preventing movement of the members. Connecting member 14 is of a standard conventional design having a terminal loop portion 15. Other designs may be used e.g. as shown in FIG. 3, wherein coupling member 16 is a specially designed resilient compression member having a pair of oppositely curved spring fingers 17 which are designed to expand by separating movement to lock in the socket of connector 32 and compress to disengage from such socket. A nonelastic stretch limiting strap 22 is located along neckstrap 10 and its ends 22a and 22b are looped around members 14 and 14' respectively and attached in any suitable fashion to members 18 and 20. The connection of strap 22 to adjustment buckle 18 provides automatic adjustment when tension adjustment of elastic strap 12 is made. Strap 22 is designed so as to limit the stretch of resilient strap 12 so a disconnecting means designed to operate with connecting member 14 can operate, e.g. as shown in FIG. 2. The stretch-limiting system of this invention effectively controls travel distance of the facebow to which it is attached, thus providing a mechanism for activating the disconnecting devices in the event of improper, inadvertent or malicious pulling on either the facebow or strap portion of the apparatus.

FIG. 2 shows a disconnecting device 24 mounted through a hook 28 of a facebow outer arch 26 and is adapted to engage the loop 15 of metal fastener 14 on a standard resilient neckstrap at 25, such neckstrap having attached a stretch-limiting strap as in FIG. 1. This system is particularly effective in providing a safety means; it is also convenient because it utilizes the stretch-limiting system in conjunction with an otherwise standard elastic strap and the disconnecting means conveniently attached to a standard facebow. There are no separate loose parts to be manipulated or misplaced.

FIG. 3 shows a disconnecting system designed to provide the same benefits as that of FIG. 2. Return-bent connector 16 includes opposed spaced fingers 17 having their end portions bent to provide concave surfaces facing each other and tip portions converging away from the return-bent portion of the connector. The return-bent connector is resilient for resilient movement of its fingers to change their spacing from a relaxed spacing when the connector is in unstressed condition. Such fingers are designed to be inserted through an opening which is formed in the end of connector block 32 (shown in cross-section) of an intermediate connecting strap 34, having therein a socket with concave sides complemental to such bent fingers, communicating with such opening and designed to receive portion fingers 17 and to connect the member 16 to the hook 28 of the outer bow 26. The relaxed spacing of the fingers in unstressed condition of the connector is different from the spacing of the fingers when their bent portions are connectibly engaged with the spaced finger-engageable surfaces of the socket in the connector block 32. To provide close coupling, the total length of the return-bent connector 16 at least does not appreciably exceed twice the maximum spacing of the finger-engageable surfaces of the socket in block 32. Strap 34 is provided with a series of longitudinally spaced holes 74, 74' therein for adjustment purposes. Strap 34 provides an additional means of adjusting tension on the facebow member 26 by selecting one of the holes of strap 34 for attachment to facebow hook 28. Strap 34 may be shortened to fit a particular patient.

The arrangement as in FIG. 3 also allows the neckstrap to stretch a certain amount until member 10 is taut. At this point, further stretching is prohibited and the shape of the connector block 32 end opening will compress resilient fingers 17 toward each other allowing them to slide from the connector block socket out of the opening. The force necessary to pull connecting member fingers 17 out of the end opening of connector block 32 can be predetermined by the cross-sectional size of member 16, the shape of member 17 and the shape of connecting member 32 end opening. Thus, if an inadvertent or malicious force is applied, the extraoral appliance will be disengaged, thereby preventing loading of the appliance as a dangerous device. The spacing between the tip portions of fingers 17 which converge away from the return-bent portion of the connector 17 when the connector is in unstressed condition is small enough so that such tip portions of the fingers can engage the opening into the socket of connector block 32. To reconnect the connector 16 and the connector block 32 after these parts have been disengaged, it is merely necessary to exert wedging pressure of the bent tip portions of fingers 17 against the opening of connector block 32 to reduce the spacing between the fingers for movement of the fingers through the opening in the connector block into connecting engagement with the finger-engaging surfaces of the socket in such block.

Figure 4:
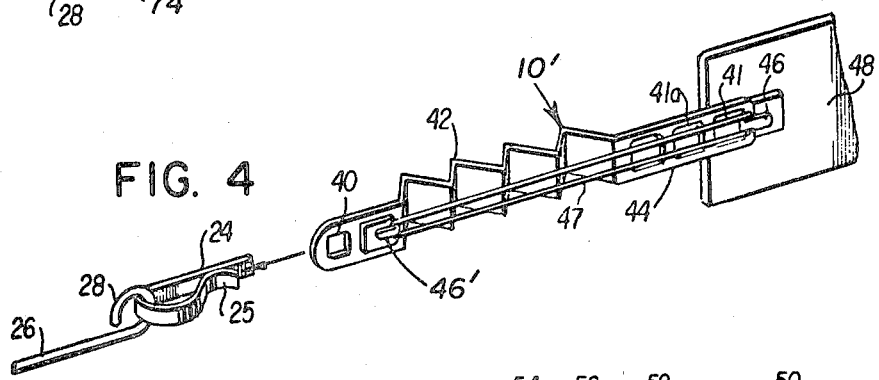
FIG. 4 is a perspective of the safety disconnect means of FIG. 2 used with a neckstrap variation in which travel is limited by an inelastic accordian strap and tension is applied by a rubber band.

FIG. 4 shows another variation in which a disconnecting device 24 is attached directly to loop 28 of facebow outer arch 26. The connecting portion 25 is adapted to engage a hole 40 or other attachment means of the stretch-limiting strap 10' which in the version presented has an accordian-like pleated section 42 and flat portion 44. A hooking means 46 attached to a nonresilient neckstrap 48 engages one of a series of apertures 41, 41a in strap 10' for attachment of the flat portion 44. A second hooking means 46' is mounted on the front portion of strap 10'. An elastic module 47 is adapted to extend between the hooks to place tension on the facebow. In a variation of this device (not shown), the accordian feature may be omitted and the elongation of holes 41, 41a increased to provide freedom for contracting by the elastic means 47 and to limit travel in the elastic expansion direction. When assembled on a patient, the apparatus so described will allow normal desirable rearward force and forward movement only until slack is removed from the system. Once taut, further force will cause disconnecting portion 25 to separate from aperture 40 or other attachment means of strap 10'. This embodiment and that described but not shown each provide an excellent means of assuring safety of rubber band tensioning neckstrap and headcap appliances.

A second group of devices shown in FIGS. 5, 6, 8 and 9 provides distinct advantages over existing spring biased headgear systems. In these embodiments, means are provided for infinitely adjusting the spring tension and subsequently the force on the facebow; the limitations of factory predetermined force ranges are thereby eliminated. Additionally, travel limiting means are provided which may also be adjusted as desired, thus again eliminating factory set travel limits. The former feature especially serves to eliminate the practitioner's need for keeping a large inventory on hand in order to satisfy commonly encountered force selection requirements. A convenient intermediate attachment means is provided and one variation of such means is also shown in FIG. 7. A variation of the force selection means is also provided in FIG. 5. These force modules are self-contained units, eliminating the need to build them in conjunction with supporting members.

Figure 6:
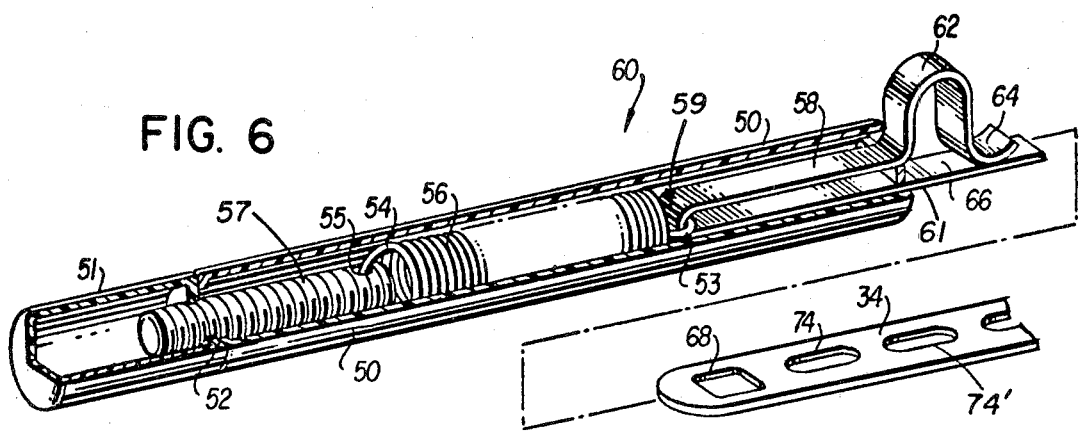
FIG. 6 is a partially cutaway perspective of a continuously variable tension adjustment device combined with a safety disconnect device.
Figure 7:
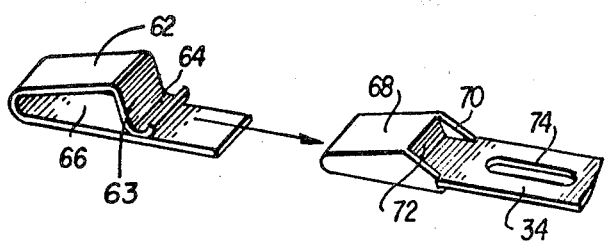
FIG. 7 is a perspective view of yet another safety disconnect device.

Referring now to FIG. 6, there is shown a tubular unit 60 having tube member 50 abutting adjustment member 51. Member 51 is preferably closed at the distal end thereof and has a threaded aperture 52 at the proximal end thereof in which is positioned adjustment screw 57. An attachment means 55 in the end of adjustment screw 57 has loop 54 of spring 56 attached thereto. On the other end of spring 56 is loop 53 which engages attachment means 59. Attachment means 59 has an upper elongated flat portion 58 terminating in a loop portion 62 and external attachment means 64 biased against lower portion 66. It will be understood that the embodiment of the attachment means and the various portions thereof may take on different forms. The important features are those which provide attachment to spring loop 53 under tension without slipping into tube 50, and stop member 61 which prevents the spring attachment member 58 from being withdrawn from tube 50 and which provides means for activating the disconnecting mechanism 64 in case of improper or inadvertent removal of the facebow from the buccal tubes. Portion 64, or a suitable variation thereof, resiliently locks to an intermediate connecting strap 34 by engaging a hole 68 therein or other suitable engagement. Application of sufficient longitudinal force on the intermediate strap 34 will disconnect the strap 34 from the engaging member 64.

Adjustment of the tension on the facebow may be accomplished by turning member 51, thereby varying the length of adjustment screw 57 within the tube 50. A capacity for infinite tension adjustment settings, within limits of the spring 56, is thus provided. Engagement of intermediate connecting strap 34 to the outer bow member is with a series of holes 74 as more clearly shown in FIG. 3. This adjustment in relationship to the amount of tension on the spring determines the travel distance of the attachment means 59 to stop 61. Hence, a versatile and effective safe headgear force system is provided.

The invention just described provides an advantage over other spring biased tensioning systems now available. This device provides the orthodontist the option of choosing the amount of travel allowed before the disconnecting mechanism becomes effective. This is accomplished by engaging the appropriate hole 74 and 74' in the intermediate attachment strap 34 with the hooked end of an outer bow.

Figure 5:
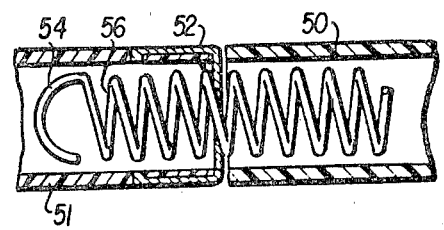
FIG. 5 is a schematic view, partially in cross-section, of a continuously variable tension adjustment device.

FIG. 5 shows a variation of the force adjusting unit of FIG. 6. The adjustment member 51 has a large opening at the end thereof and the end walls 52 are adapted to engage directly between the coils of spring 56. By rotating member 51 in relation to tube 50, the tension of the spring can be varied in a fashion similar to that described in FIG. 6. The main advantage of this variation is that the screw member 57 of FIG. 6 can be eliminated, providing simpler and less expensive manufacture. The pitch of the spring provides the same force adjustment benefits as the apparatus of FIG. 6.

FIG. 7 shows a variation of the attachment means of FIG. 6. This attachment variation includes a clip having a flat bottom plate 66, an inclined upper plate 62 formed as a return bend relative to plate 6, and a hoop segment 63 on the end of plate 65 remote from the return bend and terminating in an arcuate portion 64 at the end of the hook. The hook at the attachment is biased by the reverse bend to engage an inclined ramp section 68 on the end of strap 34 which latter has hole 74 therein. The hook can be slid up the ramp until the hook snaps over the abutment surface 72 at the higher end of ramp 68. Tab portions 70 maintain the clip in place against lateral movement. When the clip is in place, hook portion 63 bears against abutment surface 72. Although this type of arrangement is similar to that shown in FIG. 6, it provides some distinct advantages in that the force adjustment to insure release of the attachment can be conveniently controlled by altering the resiliency of the return bend connection between ramp members 65, 66 and or hook 63, the thickness and steepness of ramp 68 and the angle of abutment surface 72.

Figure 8:
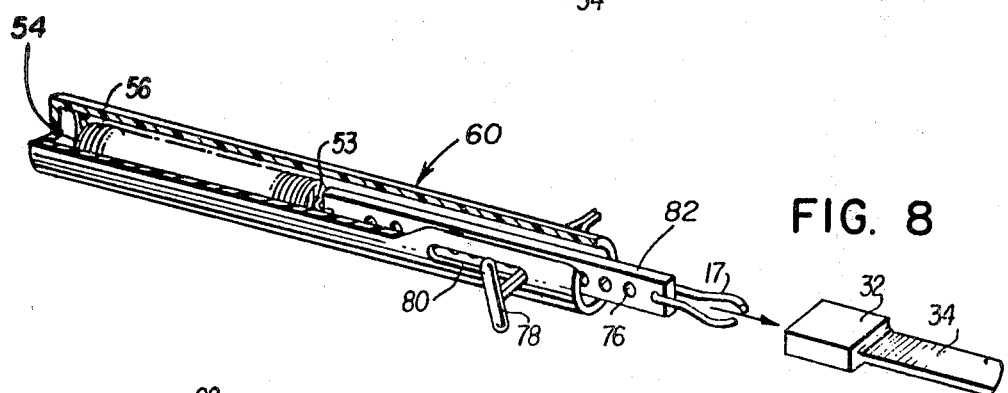
FIG. 8 is a partially cutaway perspective view of a safety release device similar to that in FIG. 3 with another variation of the tension and travel limiting means invention.
Figure 9:
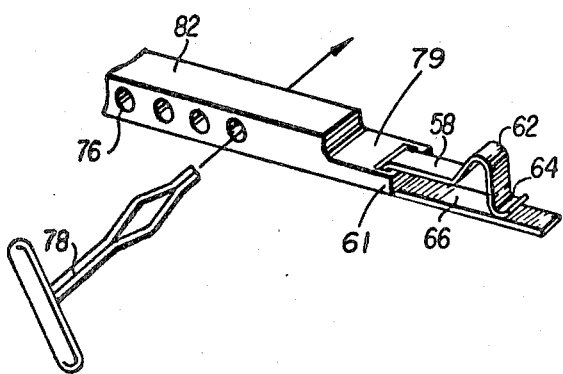
FIG. 9 is an enlarged perspective of the travel limiting means of FIG. 8 in conjunction with a safety release device of the type shown in FIG. 6.

The devices shown in FIGS. 8 and 9 provide substantially similar benefits to that of FIG. 6 with the major differences being in the mechanism for adjusting force and activating the disconnecting feature. In these embodiments, tensioning force is adjusted entirely by hole selection in the intermediate connecting strap 34, which is more clearly shown in FIG. 3. A pin device 78 inserted into a hole 76 in a linking member 82 determines the amount of free travel permitted after force selection has been so made. Attachment and disconnecting means are similar to those of FIGS. 3 and 6. The major advantage of these pin type travel limiting systems is that a wide range of forces may be easily selected without interferring with either the attachment or disconnecting system.

FIG. 8 shows a force system arrangement designed to accomplish resilient and adjustable attachment means to bias a headgear facebow. A tubular unit 60 is provided which houses the force means and other components. The spring force means 56 is secured at end 54; the other end 53 is connected to one of a series of holes in a link 82. A deformable compression release member 17 is securely attached to the outer end of link 82 and fits within a shaped socket or recess in connection block 32 of strap 34, as shown more clearly in FIG. 3. To select the amount of travel and to limit the travel distance in order to activate the compression member disconnecting portion 17, pin 78 is withdrawn. The force is selected by attaching strap 34, using the appropriate hole in strap 34, to the facebow 26 (both shown in FIG. 3) and the pin 78 is then reinserted. A slot 80 in the tube in cooperation with the pin 78 provides control of the length of travel of link 82 within slot 80 depending upon which hole 76 of link 82 pin 78 is inserted into. Any amount of pulling force which causes pin 78 to reach the travel limit allowed by slot 80 will be transferred to deformable portion 17 which will then compress and disengage strap 34 from tubular unit 60.

FIG. 9 shows a force system arrangement which is similar to that of FIG. 8 but with a safety release mechanism similar to that shown in FIG. 6. Link 82 has adjustment holes such as 76 therein through which pin 78 is adapted to extend to ride in slot 80 as shown in FIG. 8. Extension portion 79 of link 82 is adapted to receive the attachment means 58 which is substantially the same as that shown in FIG. 6. The unit can be adapted for use with an intermediate attachment strap such as 34 in FIG. 6. Adjustment and disconnecting features can be the same as for the unit of FIG. 8.

What is claimed is:

1. Orthodontic headgear apparatus for interconnection between an intraoral orthodontic device and a head or neck engageable strap and having means on at least one end thereof suitable for engaging the intraoral orthodontic device, comprising:
    limiting means having a first end connected to said strap for limiting the relative displacement between the intraoral orthodontic device and the strap, said limiting means further having a second end and including a further strap having accordian folds between said first and second ends, said further strap being nonstretchable when said folds are full expanded; and
    resilient fastening means securely engaging the intraoral orthodontic device and including means for resiliently engaging the second end of said limiting means and for releasing said second end when a predetermined relative displacement is exceeded.

2. The orthodontic headgear apparatus defined in claim 1, wherein the limiting means comprises a non-stretching strap having an aperture at the first end for engaging a hook on the strap engageable with the head or neck.

3. Safety orthodontic headgear stressing apparatus for use with an orthodontic facebow, comprising;
    a coil spring for producing the stress and having a first end and a second end;
    a tube enclosing said coil spring and having a first opening at one end;
    coupling means having a first end within said tube and securely engaged to the first end of said spring; and
    means for continuous adjustment of the relative position of the second end of said coil spring with respect to the first end of said tube.

4. In the orthodontic headgear stressing apparatus defined in claim 3, a stop bar fixedly attached to and extending chordwise across the first opening of the tube for movement-limiting engagement by the coupling means to limit stressing of the spring when the first end of the coupling means is sufficiently displaced relative to the tube in an outward direction.

5. The orthodontic headgear stressing apparatus defined in claim 3, wherein the continuous adjustment means comprises:
    a threaded shaft secured to the second end of the coil spring; and
    an adjustment member secured against movement lengthwise of the tube and having a threaded opening for engaging said threaded shaft to effect movement thereof lengthwise of the tube by rotation of said adjustment member relative to said threaded shaft.

6. The orthodontic headgear stressing apparatus defined in claim wherein the continuous adjustment means comprises an adjustment member secured against movement lengthwise of the tube and having a threaded opening for engaging the second end of the coil spring to effect movement thereof lengthwise of the tube by rotation of said adjustment member relative to the coil spring.

7. An orthodontic headgear stressing apparatus for interconnection between an intraoral orthodontic device and a head or neck engageable strap, comprising spring means that are engageable between the intraoral orthodontic device and the strap engageable with the head or neck, stationary anchor means engaging a first portion of said spring means, connector means engaging a second portion of said spring means spaced from the portion thereof engaged by said stationary anchor means and movable relative to said stationary anchor means for exerting stress on the intraoral orthodontic device, and connector movement-limiting means operable to limit movement of said connector means in a direction to increase the stress produced by said spring means and selectively adjustable to alter the limiting movement of said connector means and correspondingly to alter the maximum stress that can be transmitted from said spring means to the intraoral orthodontic device when said connector means is in its movement-limiting position established by said connector movement-limiting means.

8. In an orthodontic appliance including force-reaction means engageable with the wearer's head and/or neck, orthodontic force-applying means for applying force to a jaw and connector means connecting the force-reaction means and the force-applying means and including resilient force-producing means for producing a yieldable force applied to the force-applying means, the improvement comprising the connector means further including a disconnectible connection composed of a ramp having an abutment surface at the high end thereof and an attachment clip having a hook that can be wedged open by movement along said ramp for snap closing engagement with said abutment surface, said connection being disconnectible automatically by release of said hook from said abutment surface in response to an increase in force exerted on the connector means exceeding a predetermined limit.

9. A disconnectible connection for an orthodontic appliance comprising a ramp having an abutment surface at the high end thereof and an attachment clip having a hook that can be wedged open by movement along said ramp for snap closing engagement with said abutment surface, said connection being disengageable automatically by release of said hook from said abutment surface in response to an increase in force exerted on the connector means exceeding a predetermined limit.

10. An orthodontic headgear apparatus for use with force-applying means for applying an orthodontic force to the wearer's jaw, comprising force-reaction means engageable with the wearer's head and/or neck, and connection means for connecting the force-applying means and said force-reaction means and including a disengageable connection and a force-producing device separate from said disengageable connection, said force-producing device producing an increasing force tending to reduce the distance between said force-reaction means and the force-applying means when such means are moved farther apart, and said disengageable connection including a member having spaced finger-engageable surfaces and a return-bent connector, said return-bent connector including opposed spaced fingers having their end portions bent to provide concave surfaces facing each other and said bent finger portions being connectibly engageable with said finger-engageable surfaces, the total length of said return-bent connector at least not appreciably exceeding twice the maximum spacing of said finger-engageable surfaces.

11. The orthodontic appliance defined in claim 10, the return-bent connector being resilient for resilient movement of its fingers to change their spacing from a relaxed spacing when the connector is in unstressed condition, such relaxed spacing of the fingers being different from the spacing of the fingers when their bent portions are connectibly engaged with the spaced finger-engageable surfaces, the opposed spaced fingers being bent to provide tip portions converging away from the return-bent portion of the connector when the connector is in unstressed condition, the spacing of said finger tip portions when the connector is in unstressed condition being such as to enable wedging pressure of said converging finger tip portions against said member having spaced finger-engageable surfaces to alter the relaxed spacing of the fingers for movement thereof into connecting engagement with the finger-engageable surfaces.

12. The orthodontic headgear apparatus defined in claim 10, wherein the disengageable connection includes a socket having spaced concave finger-engageable surfaces facing each other and a restricted entrance narrower than the spacing between said concave finger-engageable surfaces, and the opposed spaced fingers are movable toward each other for insertion into said socket through said entrance and have convex surfaces engageable with said concave surfaces of said socket, respectively, by spreading of said fingers within said socket after having passed through said entrance.

* * * * *

UNITED STATES PATENT AND TRADEMARK OFFICE
CERTIFICATE OF CORRECTION

PATENT NO. : 4,402,669
DATED : September 6, 1983
INVENTOR(S) : Paul D. Frazier

It is certified that error appears in the above-identified patent and that said Letters Patent are hereby corrected as shown below:

Column 7, line 64, cancel "full" and insert ---fully---.

Column 8, line 39, after "claim" insert ---3,---.

Signed and Sealed this

Third Day of January 1984

[SEAL]

Attest:

GERALD J. MOSSINGHOFF

Attesting Officer    Commissioner of Patents and Trademarks